United States Patent [19]
Lin et al.

[11] Patent Number: 6,015,676
[45] Date of Patent: Jan. 18, 2000

[54] METHOD FOR KNOCKING OUT GENE TRANSCRIPTS BY COVALENTLY BINDING OF AN ANTI-SENSE PROBE

[75] Inventors: Shi-Lung Lin, Alhambra; Shao-Yao Ying, San Marino, both of Calif.

[73] Assignee: Epiclone Inc., Alhambra, Calif.

[21] Appl. No.: 09/127,368

[22] Filed: Jul. 31, 1998

[51] Int. Cl.$^7$ .............................. C12Q 1/68; C12P 19/34
[52] U.S. Cl. .............................. 435/6; 435/91.2; 435/810
[58] Field of Search ................................ 435/6, 91.2, 810

[56] References Cited

U.S. PATENT DOCUMENTS

| | | | |
|---|---|---|---|
| 4,599,303 | 7/1986 | Yabusaki et al. | 435/6 |
| 4,689,320 | 8/1987 | Kaji | 514/44 |
| 4,806,463 | 2/1989 | Goodchild et al. | 435/5 |
| 5,023,243 | 6/1991 | Jullis | 514/44 |
| 5,030,557 | 7/1991 | Hogan et al. | 435/6 |
| 5,110,802 | 5/1992 | Cantin et al. | 514/44 |
| 5,589,339 | 12/1996 | Hampson et al. | 435/6 |
| 5,591,575 | 1/1997 | Hampson et al. | 435/6 |
| 5,739,309 | 4/1998 | Dattagupta et al. | 536/24.5 |

FOREIGN PATENT DOCUMENTS

WO96/31523  10/1996  WIPO .

OTHER PUBLICATIONS

Falletta et. al., "Phase 1 Evaluation of Kdiaziquone in Childhood Cancer", Investigational new Drugs 8: 167–170 (1990).

Hartley et. al., DNA Cross–Linking and Sequence Selectivity of Aziridinylbenzoquinones, biochemistry 30: 11719–11724 (1991).

Hampson et.al., "Chemical Crosslinking Subtraction; A New Method for the Generation of subtractive Hybridiztion Probes", Nucleic Acids Res. 20: 2899 (1992).

Kimler et.al., "Combination of Aziridinylbenzoquiinone and Cis–platinum with Radiation Therapy in the 9L Rat Brain Tumor model", International Journal of Radiation Oncology, Biology, Physics 26:445–450 (1993).

Majumdar et.al., "Stepwise nMechanismof HIV Reverse Transcriptae: Primer Funtional of Phosphorothioate Oligodeoxynucleotide", Biochemistry 28: 1340–1346 (1989).

Matsukura et.al., "Regulation of viral expression of human immunodeficiency virus in vitro by an antisense phosphorothioate against rev (art/trs) in chronically infected cells", Proc. Natl. Acad. Sci. 86:4244–4248 (1989).

Sambrook et.al., "Molecular Clonging, 2nd Edition", Gold Spring Harbor Laboratory Press (1989).

Solomons et.al., "orgnaic Chemistry, 6th Edition", John Wiley & Sons Press (1996).

Tan et.al., "Phase 1 Study of Aziridinylbenzoquinone in Children with Cancer", Cancer Research 44:831–835 (1984).

*Primary Examiner*—John S. Brusca
*Assistant Examiner*—Andrew Wang
*Attorney, Agent, or Firm*—Raymond Y. Chan; David & Raymond

[57] ABSTRACT

The present invention provides a simple, specific and non-toxic gene knock-out method by formation of covalently bonding between modified probes and targeted sequences. When covalently modified first strand probes are hybridized with a second strand of targeted gene transcripts, certain modified bases of said first strand will interact with natural bases of said second strand to form covalent bonds by which the translation of said second strand is inhibited. Because the hybridization of said two strands generates covalent base-pairing only between their complementary homology region (s), such specificity increases the targeting efficiency of a gene knock-out system. Also, because neither a polymerase extension reaction nor a nuclease digestion can be performed through the covalently bonded region(s) of aforesaid hybrids, the present invention in conjunction with a delivery method can be used to inactivate intracellular functions of targeted nucleotide sequences, to inhibit viral infections in vivo and to increase binding stability of antisense drugs in a gene therapy.

53 Claims, 3 Drawing Sheets

FIG.2(a)

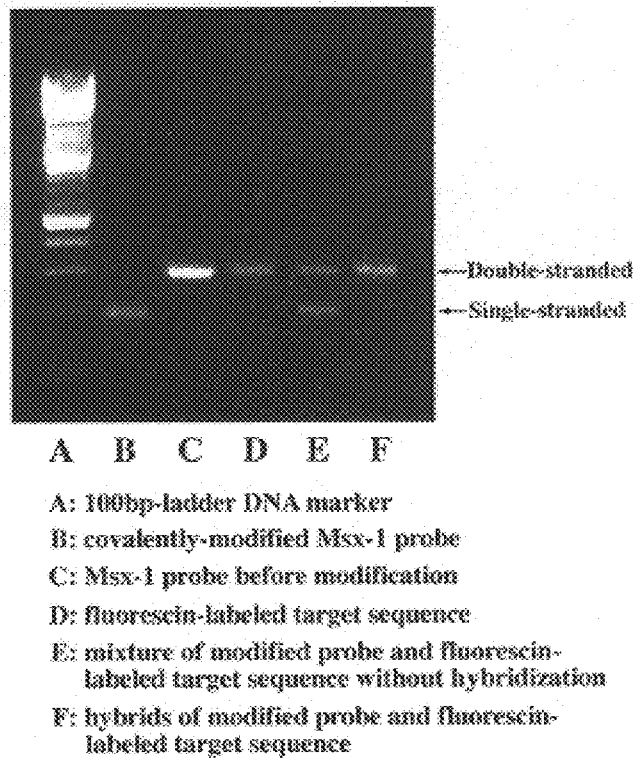

A: 100bp-ladder DNA marker
B: covalently-modified Msx-1 probe
C: Msx-1 probe before modification
D: fluorescin-labeled target sequence
E: mixture of modified probe and fluorescin-
   labeled target sequence without hybridization
F: hybrids of modified probe and fluorescin-
   labeled target sequence

FIG.2(b)

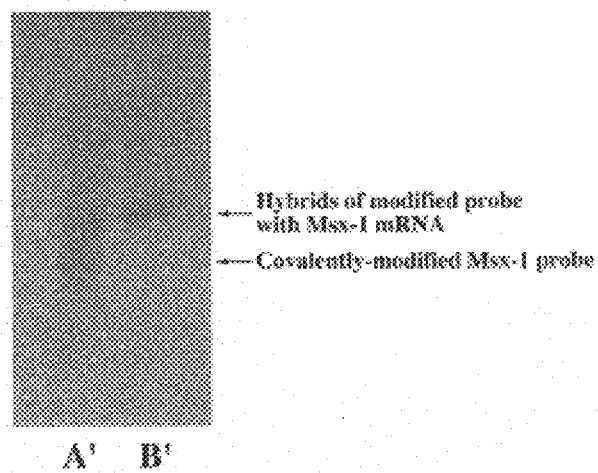

A': hybrids of Msx-1 transcript with labeled,
    covalently-modified probe

B': mRNAs isolated from Msx-1 transfected
    cells with modified anti-Msx-1 treatment B": PCR amplification of nonmodified natural hybrid duplexes C": PCR amplification of covalently modified hybrid duplexes

METHOD FOR KNOCKING OUT GENE TRANSCRIPTS BY COVALENTLY BINDING OF AN ANTI-SENSE PROBE

BACKGROUND OF THE INVENTION

1. Field of the Invention

The present invention generally relates to the field of methods of gene knock-out with interstrand binding between a specific probe and its target sequence. More particularly, the present invention relates to the field of improved methods for knocking out specific gene expression by covalently bonding formation between a gene transcript and its anti-sense probe.

2. Description of the Prior Art

The following references are pertinent to this invention:

1. Falletta et.al., "Phase 1 Evaluation of Diaziquone in Childhood Cancer", *Investigational New Drugs* 8: 167–170 (1990).
2. Hartley et.al., "DNA Cross-linking and Sequence Selectivity of Aziridinylbenzoquinones", *Biocldenmistry* 30: 11719–11724 (1991).
3. Hampson et.al., "Chemical Crosslinking Subtraction; A New Method for the Generation of subtractive hybridization probes", *Nucleic Acids Res.* 20: 2899 (1992).
4. Kimler et.al., "Combination of Aziridinylbenzoquinone and Cis-platinum with Radiation Therapy in the 9L Rat Brain Tumor Model", *International Journal of Radiation Oncology, Biology, Physics* 26: 445–450 (1993).
5. Majumdar et.al., "Stepwise Mechanism of HIV Reverse Transcriptase: Primer Function of Phosphorothioate Oligodeoxynuclcotide", *Biochemistry* 28: 1340–1346 (1989).
6. Matsukura et.al., "Regulation of viral expression of human immunodeficiency virus in vitro by an antisense phosphorothioate against rev (art/trs) in chronically infected cells", *Proc. Natl. Acad. Sci.* 86: 4244–4248 (1989).
7. Sambrook et.al., *"Molecular Cloning, 2nd Edition"*, Cold Spring Harbor Laboratory Press (1989).
8. Solomons ct.al., *"Organic Chemistry, 6th Edition"*, John Wiley & Sons Press (1996).
9. Tan et.al., "Phase 1 Study of Aziridinylbenzoquinone in Children with Cancer", *Cancer Research* 44: 831–835 (1984).
10. U.S. Pat. No. 4,599,303 issued to Yabusaki et.al.
11. U.S. Pat. No. 4,689,320 issued to Kaji et.al.
12. U.S. Pat. No. 4,806,463 issued to Goodchild et.al.
13. U.S. Pat. No. 5,023,243 issued to Tullis et.al.
14. U.S. Pat. No. 5,030,557 issued to Hogan et.al.
15. U.S. Pat. No. 5,110,802 issued to Contin et.al.
16. U.S. Pat. No. 5,589,339 issued to Hampson et.al.
17. U.S. Pat. No. 5,591,575 issued to Hampson et.al.
18. U.S. Pat. No. 5,739,309 issued to Dattagupta et.al.

Anti-sense sequences of certain gene transcript have been widely used as probes in gene knock-out systems to detect specific gene functions as well as to perform clinical therapy for many years. Based on the hydrogen-bonding of natural nucleotide sequences, many kinds of anti-sense probes were designed to interfere normal functions of certain gene tran- script (mRNA) by increasing the binding stability of probe-mRNA hybrids. These anti-sense probes include sequence-specific "helper" oligonucleotides (U.S. Pat. No. 5,030,557 by Hogan et.al.; U.S. Pat. No. 5,023,243 by Tullis et.al.; U.S. Pat. No. 4,689,320 by Kaji et.al.), multiple-targeting oligo-nucleotides (U.S. Pat. No. 4,806,463 by Goodchild et.al.), methylphosphorate-linked oligonucleotides (U.S. Pat. No. 5,110,802 by Contin et.al.) and phosphorothioate-linked oligonucleotides (Majumdar et.al., *Biochemistry* 28: 1340 (1989); Matsukura et.al., *Proc. Natl. Acad. Sci.* 86: 4244 (1989); U.S. Pat. No. 5,739,309 by Dattagupta et.al.). Some of special chemical linkages used in aforementioned anti-sense probes are designed for reducing nuclease digestion of probes and increasing sequence-specific targeting. However, all these anti-sense technologies specifically bind to targeted sequences through hydrogen-bonding affinity, resulting a requirement of exceedingly high concentration treatments for biological effects.

On the other hand, the ability to form covalently bonding between two nucleotide sequences has permitted a fully complete subtraction of undesired sequences through hybridizative binding. Unlike hydrogen-bonding formed between natural nucleotide sequences, because the covalent bond is one of the strongest and most heat-stable interactions between molecules, covalently bonding of two nucleotide sequences can sustain most harsh treatments or conditions, such as denaturing, salting, desalting, enzyme digestion and some redox reaction. Based on such feature, some methods have been developed either to perform anti-sense chemotherapy for killing cancer cells as well as viruses or to detect unique gene expressions with cross-linking chemicals by which unwanted homologues were covalently eliminated. One of the most commonly used cross-linking chemicals to accomplish such sequence-selective elimination is aziridi-nylbenzoquinone (AZQ)-class agent (Hartley et.al., *Biochemistry* 30: 11719–11724 (1991)), involving a cross-linking between guanine (G) and cytosine (C).

In clinics, AZQ-class agents have been tested as a chemotherapy drug for treating several cancers, such as brain tumors in rat (Kimler et.al., *International Journal of Radiation Oncology, Biology, Physics* 26: 445–450 (1993)) and phase I childhood cancers in human (Falletta et.al., *Investigational New Drugs* 8: 167–170 (1990); Tan et.al., *Cancer Research* 44: 831–835 (1984)). By enhancing the binding, stability of genomic double-stranding conformations, the AZQ-clke molecules w ere expected to reduce the replication of the cancer cells. However, the nonspecific cross-linking feature of AZQ-like molecules also causes significant toxicity to normal cells. Thus, the use of AZQ-like molecules in an anti-sense gene therapy seems unpractical now. Since the lack of sequence-specific targeting capability is an unsolved problem in vivo, in vitro methods become the only feasible way to apply AZQ-cike cross-linking molecules for subtracting unwanted genes.

Prior art attempts at in vitro subtraction of targeted sequences with covalently bonding, such as U.S. Pat. No. 5,589,339 and U.S. Pat. No. 5,591,575 to Hampson et.al., uses te cross-linking agents to covalently subtract unwanted sequences from compared libraries. Unfortunately, although the AZQ-like cross-linking molecules successfully achieve the completion of homologue subtraction, such subtraction only occurs in test tubes with single-stranded oligonucleotide samples. Other prior art attempts at sequence-targeting, such as U.S. Pat. No. 4,599,303 to Yabusaki et.al., uses azide-like cross-linking molecules to detect isolated targets which are unavailable in living cells. Therefore, in addition to the significantly cytotoxic nature of cross-linking molecules, the disadvantages of these methods exclude the possibility to subtract specific gene expression from living cells.

In summary, it is desirable to have a simple, specific and nontoxic gene knock-out method for increasing binding efficiency of an anti-sense probe to its targeted gene transcript, of which the results may contribute to an investigation of new gene functions, a diagnosis for inherent problems, or an anti-sense therapy for diseases.

SUMMARY OF THE INVENTION

The present invention is a novel gene knock-out method which provides a simple, specific and nontoxic covalently bonding formation between a gene transcript and its anti-sense probe.

Described in detail, a preferred embodiment of the present invention method includes the following steps:

a. providing a first strand of nucleotide sequences as complementary probes to a targeted gene transcript, wherein said first strand of nucleotide sequences is single-stranded and carboxylated in the nucleotide base structures of said first strand of nucleotide sequences;

b. preserving said first strand of nucleotide sequences in a delivery vector, wherein said delivery vector transports said first strand of nucleotide sequences into cells;

c. contacting said first strand of nucleotide sequences with a second strand of gene transcripts in said cells, wherein said second strand of gene transcripts contains natural amino-groups in the nucleotide base structures of said second strand of gene transcripts; and d. permitting said first strand of nucleotide sequences and said second strand of gene transcripts to form double-stranded hybrid duplexes comprising covalently bonding between the carboxyl-groups of said first strand and the amino-groups of said second strand.

To increase the binding force of hybrid duplexes in cells, the first strand of nucleotide sequences is preferably carboxylated on the C-4 of uracil/thymine or C-5/C-6 of pyrimidines in order to covalently bonding with the amino-groups of the targeted gene transcripts on the C-6 of adenine or C-6/C-2 of purines respectively. Most preferably, the carboxylated group is on the C-5 of uracil which covalently bonds to the C-6 amino-group of adenine. Advantageously, the covalently bonded hybrid duplexes are not separated during translation, resulting a temporary halt for the protein generation of this gene.

In another aspect of this embodiment, for preventing the reassociation of undesired first strand sequences, the amino-groups of the first strand sequences are preferably removed by blocking agents. Preferably, the blocking agent is alkaline acetic chloride reagent which converts the activating amino-groups of purines into inactive acetamido-groups for preventing bonding formation between interstrand nucleotide sequences. Advantageously, the single-stranded and modified first strand probes are only covalently hybridized with the complementary homologues of the targeted gene transcript in cells, resulting in an increase of covalently bonding efficiency.

The present invention also includes a kit for performing an improved gene knock-out method with covalently bonding formation between a gene transcript and its anti-sense probe, comprising some or all of the following components:

a. an amino-blocking reagent which makes said first strand of nucleotide probes single-stranded;

b. a carboxylating reagent which generates said carboxyl-groups on the nucleotide base structures of said first strand probes; and c. a delivery vector which permits hybridization of said first strand probes and said second strand gene transcripts in said cells to form said covalently bonded hybrid duplexes.

Preferably, the amino-blocking agent is acetic anhydride reagent or alkaline acetic chloride reagent, and the carboxylating agent is hot alkaline potassium permanganate reagent. Preferably, the delivery vector is a liposome-like molecule with minimal cytotoxicity.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated:

FIGS. 2a–2c illustrate the results of example 2 and 3 of the present invention.

DESCRIPTION OF THE PREFERRED EMBODIMENT

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

The present invention is directed to an improved method of gene knock-out by covalently bonding formation between interstrand nucleotide sequences, particularly between certain specific gene transcript and its anti-sense probe. This method is primarily designed for inhibiting a specific gene expression in cells, preventing viral infections through inactive bonding of viral genome, and increasing stability of antisense probe targeting during gene therapy. The purpose of the present invention relies on the inhibitory force of the covalently bonding between certain specific gene transcript and its anti-sense probes, resulting in no such gene translation in cells. The preferred version of the present invention is based on: single-stranding of probe sequences as anti-sense, covalent modification of the single-stranded probes, and in-cell-hybridization of the modified probes with targeted gene transcript(s) to form covalently bonding within some specific base-pairs. In conjunction with a delivery vector for intracellular transportation, a very small amount of probes can be used as anti-sense for adjusting certain gene expression.

As used herein, the covalent modification refers to a series of chemical reactions by which the capability of covalently bonding with natural nucleotide sequences is render to the modified probe sequences and is generated herein by using single-stranding reagent(s) and carboxylating reagent(s). The single-stranding reagent refers to chemicals which can block or remove the amino-group of a purine base, such as acetic anhydride and alkaline acetic chloride. And, the carboxylating reagent refers to chemicals that can generate carboxyl-groups on the base structure of a probe sequence, such as sodium cyanide/sulfuric acid mixture and hot alkaline potassium permanganate. The homologue refers to nucleotide sequences which share high similarity in the order arrangement of their certain domains.

Figure 1A:
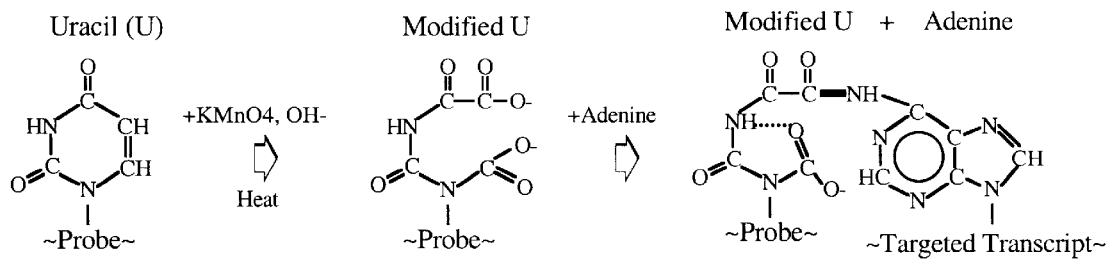
FIGS. 1a–1b illustrate the preferred covalent modifications.
Figure 1B:
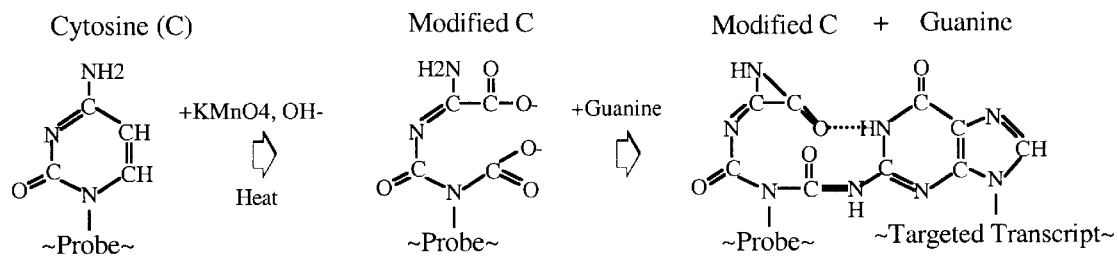

The advantages of using covalently modified nucleotide sequences as antisense probes are as follows: First, during a targeting hybridization, the affinity between homologues can be greatly enhanced by the covalent bonding. For example, the carboxyl-group on the C-5/C-6 of modified pyrimidines can form peptide-like bonding with the amino-group on the C-6/C-2 of natural purines respectively (FIGS. 1a–1b). Such covalently bonding between complementary homologues fully inhibits any further reaction of the targeted sequences, resulting knocking out the functional activity of such nucleotide sequences. Second, the modified probes are primarily single-stranded, resulting in high binding efficiency between the modified and natural sequences rather than between two modified strands. Third, because the covalently bonding is an internal affinity either between natural adenine and modified uracil/thymine or between guanine and modified cytosine, this kind of pairing property significantly increases the specificity of covalently bonding by which only highly matched homologues can form hybrid duplexes.

Because the covalent modification can be greatly facilitated by using nucleotide analog-containing sequences, the probe sequences are preferably incorporated with certain nucleotide analog(s). For example, when 2'-deoxy-deoxyuridine triphosphate instead of deoxythymidine triphosphate is used to generate the modified antisense probes, the carboxylation will occur only on the C-4 of uracil rather than the C-2 which is a unwanted reaction. Preferably, here listed below are some examples of the preferred analog formula:

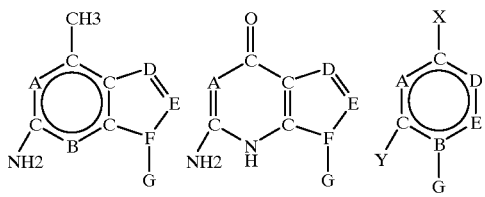

in which A, B, D, E and F can be either a N or a CH group, G is a 2'-deoxy-D-ribose triphosphates, and X is a methyl group while Y is a H group and vice versa. Such incorporation is generally achieved by a polymerase-chain-reaction, a template extension of DNA polymerase, a special plasmid cloning or an in-vitro transcription. Although the adenine (A), guanine (G), cytosine (C), thymine (T) and uracil (U) were used in the generation of covalently modified probes, any nucleotide derivative or its analog capable of being incorporated and modified into probes for the purpose of covalently bonding between sequence homologues is within the scope of the present invention.

In order to prevent the formation of self binding between two modified probes, the amino-groups of probe sequences must be blocked or removed. Such blocking reaction is preferably carried out by acetylating the amino-group of purines into an inactive acetamido-group which is incapable of interacting with a carboxyl-group of the modified probe, resulting in single-stranding of the probe. Acetic anhydride and alkaline acetic chloride are major ingredients in the preferred blocking reagent of the present invention. Because the single-stranded probe exposes its base structures, a carboxylating agent can then oxidize the alkene, carbonyl or sometimes methyl group into carboxyl-groups (Solomons et.al., 1996) which gradually form peptide-like bonding with the activating amino-group of a non-modified natural nucleotide sequence. Hot alkaline potassium permanganate is a preferred major ingredient in the carboxylating reagent of the present invention based on its nucleophilic addition.

After aforementioned covalent modification, the modified probe is then mixed with a delivery vector, preferably a liposomal compound which capsules the probe for penetrating through cell membranes. In the preferred embodiment, a preferred concentration of the modified probe in a cultural medium is from about 0.1 μg/ml to about 10 μg/ml, most preferably, about 1.2 μg/ml to 2 μg/ml. If the concentration is too high in transfected cells, the modified probe will covalently bind not only to the targeted gene transcript but also to its genomic homology region, resulting no replication of the transfected cells. If the concentration is too low, the modified probe will be not sufficient to block most of the gene transcript, resulting in a failure of gene knock-out system. The optimal concentration will vary depending on the transcriptional activity of targeted genes.

When the modified probe is hybridized with its targeted transcript in cells, early hydrogen-bonding between complementary sequences will hold their interstrand distance long enough to form covalently bonding. Since such covalently bonded transcript is permanently not available for translation, the present invention can be used to inhibit protein synthesis of certain gene and therefore achieves the same effects of gene knock-out. Unlike transgenic knock-out mice technology, the present invention does not require animal sacrifice, and even better, it can be performed in small tissue culture which provides more humanity for research. Furthermore, when compared to a dominant negative knock-out system with viral transfection, the present invention provides a more consistent result without the risk of viral contamination. The information so obtained also provides further understanding of a variety of diseases, physiological phenomena, and genetic functions.

Alternatively, the present invention may be extended to perform in-situ-hybridization as well as antisense gene therapy. Because covalently bonded hybrid duplexes are highly resistant to nuclease digestion, when a covalently modified probe is labeled and used in an in-situ-hybridization, its targeted nucleotide sequence will be clearly identified in tissues as well as in wholemounts due to a wash-proof bonding formed between the probe and the target. By the same token, if the covalently modified probes are used as in vivo drugs of an antisense gene therapy, the targeted gene which we want to inactivate will be shut down in that transcription and translation can not proceed through the covalently bonded region. Examples as mentioned here will be developed into continuity in part of the present invention and is not intended in any way to limit the broad features or principles of the present invention.

According to the high efficiency of covalent modifications in the preferred embodiment of the present invention, the labor- and time-consuming factors can be reduced to the minimum. Also, the preparation of the covalently modified nucleotide sequences is cheaper and more efficient than that of other modified sequences in previous methods. Most importantly, such covalent modification can be carried out continuously in microtubes with only few changes of buffers. Taken together, these special features make the present invention as fast, simple, and inexpensive as a kit for generating covalently modified probes to perform gene knock-out in cells.

Although certain preferred embodiments of the present invention have been described, the spirit and scope of the invention is by no means restricted to what is described above. For example, within the general framework of (a) one or more specific probes used; (b) one or more nucleotide analogs incorporated into probes; (c) one or more chemical reagents used to complete covalent modification; (d) one or more kinds of delivery vectors used to transport covalently modified probes into cells, there is a very large number of permutations and combinations possible, all of which are within the scope of the present invention.

EXAMPLE 1

Covalent Modification of First Strand Nucleotide Probes

Figure 2C:
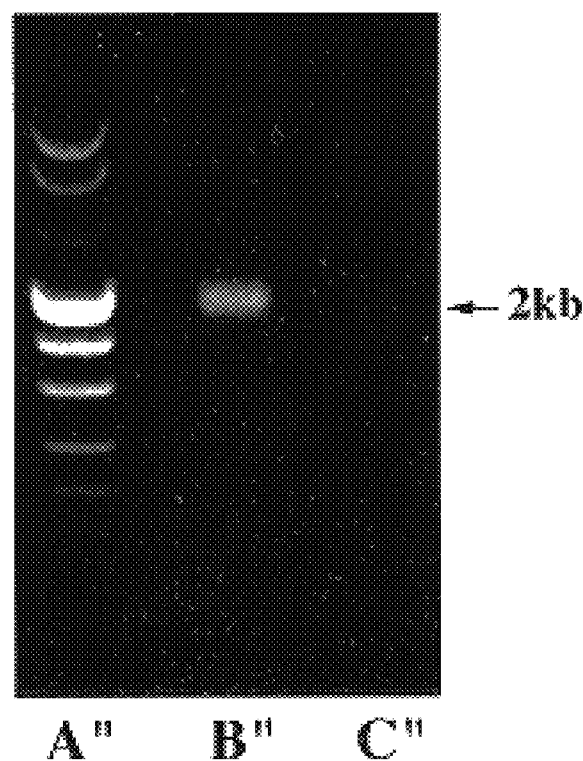

Msx-1 probe was prepared from inserted pBluescript II KS phagemid (Stratagene) by XbaI plus EcoRI restrictions, and purified by agarose gel electrophoresis. After 10 μg of the Msx-1 probe (lane C of FIG. 2(a)) was recovered by Gel Extraction kit (Qiagen), alkaline acetic chloride reagent (20 μl) was added (5 min, 95° C.) to make Msx-1 probe single-stranded by acetylating its amino-groups. Following a recollection of the single-stranded probe by Micropure™-EZ columns (Minipore), alkaline potassium permanganate reagent (20 μl) was then added (5 min, 85° C.) to generate carboxyl-groups on the C-5/C-6 of uracil/cytosine which can form covalently bonding with amino-groups on the C-6/C-2 of adenine/guanine of natural oligonucleotides respectively. The carboxylated Msx-1 probe was finally recollected by Micropure™-EZ column and resuspended in total 10 μl of 20 mM N-[2-hydroxyethyl]piperazine-N'-[2-ethanesulfonic acid] (HEPES) buffer.

EXAMPLE 2

Transfection of the First Strand Probe into Cells

Covalently modified Msx-1 probe (8 μg as shown in lane B of FIG. 2(a)) was mixed with 50 μl of DOTAP liposome (1 mg/ml, Boehringer Mannheim) and applied to 100 mm diameter culture dishes which contain 50% full of chicken embryo fibroblasts (CEF). The CEF grown in HBSS medium were transfected by overexpression of full-length Msx-1 gene (~1 kb) as a target sequence for aforementioned probe. After 24-hour incubation, 60% of the probe-containing liposome was uptaken by the CEF. And after two-day incubation, 100% of the probe-containing liposome was uptaken by the CEF. An in-vitro test as shown in FIG. 2(a) indicates that the covalently modified Msx-1 probe without liposomal treatment fails to bind with its transfected target sequence (two bands in lane E) whereas the same procedure with liposomal treatment shows a complete hybridization (only one upper band in lane F).

EXAMPLE 3

Hybridization of the First Strand Probe with Targeted Nucleotide Sequences

For in-cell hybridization, the mRNAs of above transfected CEF cells were isolated by Oligotex Direct mRNA kit (Qiagen) after 24-hour incubation with the probe-containing liposome. 2 μg of mRNAs were separated by electrophoresis through 1% formaldehyde-agarose gel and transferred to nylon membrane (Schleicher & Schuell) by another horizontal electrophoresis. Since the modified Msx-1 probe was also labeled by [$^{33}$P-α] dATP (Amersham), hybrid duplexes of the modified Msx-1 probe to its targeted gene transcript can be detected by overnight exposure of BioMax film (Kodak) as shown in the lane B' of FIG. 2(b). Only a labeled 2 kb hybrid duplex seen on the membrane indicates that the modified Msx-1 probe (1 kb) was completely hybridized with intercellular Msx-1 gene transcript (~1 kb). For comparison, the lane A' of FIG. 2(b) demonstrates an in-vitro range from the single-stranded modified probe (1 kb, lower band) to the complete hybrid duplexes (2 kb, upper band). Furthermore, the 2 kb hybrid duplex has been isolated and tested in a polymerase chain reaction (PCR) with Msx-1 specific primers, indicating no amplification due to its covalently bonding (lane C" of FIG. 2(c)).

The present invention h as been described with reference to particular preferred embodiments; however, the scope of this invention is defined by the attached claims and should be constructed to include reasonable equivalents.

Defined in detail, the present invention is a gene knock-out method which provides covalently base-pairing formation between a targeted gene transcript and its anti-sense probe, comprising the steps of:

a. providing a first strand of nucleotide sequences as complementary probes to a targeted gene transcript, wherein said first strand of nucleotide sequences is single-stranded and carboxylated in the nucleotide base structures of said first strand of nucleotide sequences;

b. preserving said first strand of nucleotide sequences in a delivery vector, wherein said delivery vector transports said first strand of nucleotide sequences into cells;

c. contacting said first strand of nucleotide sequences with a second strand of gene transcripts in said cells, wherein said second strand of gene transcripts contains natural amino-groups in the nucleotide base structures of said second strand of nucleotide sequences;

d. permitting said first strand of nucleotide sequences and said second strand of gene transcripts to form double-stranded hybrid duplexes comprising covalently base-pairing between the carboxyl-groups of said first strand and the amino-groups of said second strand; and e. whereby said method provides a simple, specific and nontoxic covalently bonding formation between said two strands of nucleotide sequences for gene knock-out.

Alternatively defined in detail, the present invention is a kit for performing said gene knock-out method with covalently base-pairing formation between a gene transcript and its anti-sense probe, comprising some or all of the following components:

a. an amino-blocking reagent which makes said first strand of nucleotide probes single-stranded;

b. a carboxylating reagent which generates said carboxyl-groups on the nucleotide base of said first strand probes;

c. a delivery vector which permits hybridization of said first strand probes and said second strand gene transcripts in said cells to form said covalently bonded hybrid duplexes; and d. whereby said kit provides a simple, specific and non-toxic covalently base-pairing formation between said two strands of nucleotide sequences for gene knock-out.

Defined broadly, the present invention is a sequence-targeting method which provides covalently bonding formation between a modified nucleotide probe and its intercellular target sequence, comprising the steps of:

a. providing a first strand of nucleotide sequences as complementary probes to a targeted intercellular nucleotide sequence, wherein said first strand of nucleotide sequences is single-stranded and covalently modified in the base structures of said first strand of nucleotide sequences;

b. transporting said first strand of nucleotide sequences into cells with a delivery method, wherein said delivery method makes said first strand of nucleotide sequences become intracellular;

c. contacting said first strand of nucleotide sequences with a second strand of targeted nucleotide sequences in said cells, wherein said second strand of targeted nucleotide sequences contains natural base structures;

d. permitting said first strand and said second strand of nucleotide sequences to form covalently bonding between the modified base structures of said first strand and the natural base structures of said second strand of nucleotide sequences; and e. whereby said method provides a simple, specific and nontoxic covalently bonding formation between said two strands of nucleotide sequences for gene knock-out.

Alternatively defined broadly, the present invention is a kit for performing said sequence-targeting method with covalently bonding formation between a modified nucleotide probe and its intercellular target sequence, comprising:

a. a set of chemical reagents which make said first strand of nucleotide sequences single-stranded and modified for covalently bonding with said second strand of targeted nucleotide sequences;

b. a delivery method which permits hybridization of said first strand and said second strand sequences in said cells to form said covalently bonded hybrid duplexes; and c. whereby said kit can be used to provide a simple, specific and nontoxic covalently bonding formation between said two strands of nucleotide sequences for gene knock-out.

Of course the present invention is not intended to be restricted to any particular form or arrangement, or any specific embodiment disclosed herein, or any specific use, since the same may be modified in various particulars or relations without departing from the spirit or scope of the claimed invention hereinabove shown and described of which the apparatus shown is intended only for illustration and for disclosure of an operative embodiment and not to shown all of the various forms or modifications in which the present invention might be embodied or operated.

The present invention has been described in considerable detail in order to comply with the patent laws by providing full public disclosure of at least one of its forms. However, such detailed description is not intended in any way to limit the broad features or principles of the present invention, or the scope of patent monopoly to be granted.

What is claimed is:

1. A method of performing a gene knock-out technology by covalent bond formation between a targeted gene transcript and an anti-sense probe thereof, comprising the steps of:

a. providing a first strand of nucleotide sequences as a plurality of complementary probes to a targeted gene transcript, wherein said first strand of nucleotide sequences is single-stranded and carboxylated in the nucleotide base structures of said first strand of nucleotide sequences;

b. preserving said first strand of nucleotide sequences in a delivery vector, wherein said delivery vector transports said first strand of nucleotide sequences into cells;

c. contacting said first strand of nucleotide sequences with a second strand of gene transcripts in said cells, wherein said second strand of gene transcripts contains natural amino-groups in the nucleotide base structures of said second strand of gene transcripts; and permitting said first strand of nucleotide sequences and said second strand of gene transcripts to form double-stranded hybrid duplexes comprising covalently base-pairing between the carboxyl-groups of said first strand and the amino-groups of said second strand; so as to provide covalent bond formation between said two strands of nucleotide sequences for gene knock-out.

2. The method as defined in claim 1, before step (a); further comprising the step of nucleotide-analog incorporation into said first strand of nucleotide sequences.

3. The method as defined in claim 2 wherein said nucleotide analogs are incorporated into said first strand of nucleotide sequences by a DNA polymerase.

4. The method as defined in claim 3 wherein said DNA polymerase is Taq polymerase.

5. The method as defined in claim 2 wherein said nucleotide analogs are deoxyuridine triphosphate derivatives.

6. The method as defined in claim 1 wherein said first strand of nucleotide sequences is single-stranded by an amino-blocking agent and then modified by a carboxylating agent in order to generate carboxyl-groups on the nucleotide base structures of said first strand of nucleotide sequences.

7. The method as defined in claim 6 wherein said amino-blocking agent is an acetic anhydride reagent.

8. The method as defined in claim 6 wherein said amino-blocking agent is an alkaline acetic chloride reagent.

9. The method as defined in claim 6 wherein said carboxylating agent is an alkaline potassium permanganate reagent.

10. The method as defined in claim 1 wherein said double-stranded hybrid duplexes are formed by complementary homologues between said first strand of nucleotide sequences and said second strand of gene transcripts.

11. The method as defined in claim 1 wherein said first strand of nucleotide sequences is in a final concentration from about 0.1 $\mu$g/ml to about 10 $\mu$g/ml.

12. The method as defined in claim 11 wherein said concentration is about 1.2 $\mu$g/ml to 2 $\mu$g/ml.

13. A kit for performing a gene knock-out method by covalent bond formation between a gene transcript and an anti-sense probe thereof, comprising:

a. an amino-blocking reagent which makes a first strand of nucleotide probes single-stranded;

b. a carboxylating reagent which generates carboxyl-groups on the nucleotide base structures of said first strand probes; and c. a delivery vector which permits hybridization of said first strand probes to a second strand of gene transcripts in cells to form covalently bonded hybrid duplexes;

whereby said kit provides covalent bond formation between said two strands of nucleotide sequences for gene knock-out.

14. The kit as defined in claim 13, further comprising nucleotide analogs for incorporating into said first strand of nucleotide probes.

15. The kit as defined in claim 14 wherein said nucleotide analogs are deoxyuridine triphosphate derivatives.

16. The kit as defined in claim 14 wherein said nucleotide analogs are incorporated into said first strand probes by a DNA polymerase.

17. The kit as defined in claim 16 wherein said DNA polymerase is Taq polymerase.

18. The kit as defined in claim 16 wherein said DNA polymerase is *E. coli* DNA polymerase 1 which contains Klenow fragment activity.

19. The kit as defined in claim 13 wherein said amino-blocking agent is an acetic anhydride reagent.

20. The kit as defined in claim 13 wherein said amino-blocking a gent is an alkaline acetic chloride reagent.

21. The kit as defined in claim 13 wherein said carboxylating agent is an alkaline potassium permanganate reagent.

22. The kit as defined in claim 13 wherein said delivery vector is a liposomal transfection reagent.

23. The kit as defined in claim 22 wherein said liposomal transfection reagent contains cationic liposomes.

24. The kit as defined in claim 13 wherein said first strand of nucleotide probes is in a final concentration from about 0.1 µg/ml to about 10 µg/ml.

25. The kit as defined in claim 24 wherein said concentration is about 1.2 µg/ml to 2 µg/ml.

26. A method of performing a sequence-targeting technology which provides covalent bond formation between a nucleotide probe and an intercellular target sequence thereof, comprising the steps of:
   a. providing a first strand of nucleotide sequences as a plurality of complementary probes to a targeted intercellular nucleotide sequence, wherein said first strand of nucleotide sequences is single-stranded and covalently modified in the base structures of said first strand of nucleotide sequences;
   b. transporting said first strand of nucleotide sequences into cells with a delivery method, wherein said delivery method makes said first strand of nucleotide sequences become intracellular;
   c. contacting said first strand of nucleotide sequences with a second strand of targeted nucleotide sequences in said cells, wherein said second strand of targeted nucleotide sequences contains natural base structures; and
   d. permitting said first strand and said second strand of nucleotide sequences to form covalently bonding between the modified base structures of said first strand and the natural base structures of said second strand of nucleotide sequences; so as to provide covalent bond formation between said two strands of nucleotide sequences for knocking out the function of said second strand sequences.

27. The method as defined in claim 26, before step (a); further comprising the step of nucleotide-analog incorporation into said first strand of nucleotide sequences.

28. The method as defined in claim 27 wherein said nucleotide analogs are incorporated into said first strand of nucleotide sequences by a DNA polymerase.

29. The method as defined in claim 28 wherein said DNA polymerase is Taq polymerase.

30. The method as defined in claim 28 wherein said nucleotide analogs are deoxyuridine triphosphate derivatives.

31. The method as defined in claim 26 wherein said first strand of nucleotide sequences is single-stranded and modified by chemical reagents in order to generate said covalent bond with said second strand of nucleotide sequences.

32. The method as defined in claim 31 wherein said chemical reagents contain acetic anhydride.

33. The method as defined in claim 31 wherein said chemical reagents contain alkaline acetic chloride.

34. The method as defined in claim 31 wherein said chemical reagents contain alkaline potassium permanganate.

35. The method as defined in claim 26 wherein said second strand of targeted nucleotide sequences is an abnormally functional gene transcript.

36. The method as defined in claim 26 wherein said second strand of targeted nucleotide sequences is a mutant gene and its transcript.

37. The method as defined in claim 26 wherein said second strand of targeted nucleotide sequences is a viral gene and its transcript.

38. The method as defined in claim 26 wherein said covalent bond is formed between complementary homologues of said first strand and said second strand of nucleotide sequences.

39. The method as defined in claim 26 wherein said first strand of nucleotide sequences is in a final concentration from about 0.1 µg/ml to about 10 µg/ml.

40. The method as defined in claim 39 wherein said concentration is about 1.2 µg/ml to 2 µg/ml.

41. A kit for performing a sequence-targeting method by covalent bond formation between a nucleotide probe and an intercellular target sequence thereof, comprising:
   a. a set of chemical reagents which make a first strand of nucleotide sequences single-stranded and modified for covalent bonding with a second strand of targeted nucleotide sequences; and
   b. a delivery method which permits hybridization of said first strand and said second strand sequences in cells to form covalently bonded hybrid duplexes;
   whereby said kit provides covalent bond formation between said two strands of nucleotide sequences for targeted sequence knock-out.

42. The kit as defined in claim 41, further comprising nucleotide analogs for incorporating into said first strand of nucleotide sequences.

43. The kit as defined in claim 42 wherein said nucleotide analogs are deoxyuridine triphosphate derivatives.

44. The kit as defined in claim 42 wherein said nucleotide analogs are incorporated into said first strand of nucleotide sequences by a DNA polymerase.

45. The kit as defined in claim 44 wherein said DNA polymerase is Taq polymerase.

46. The kit as defined in claim 44 wherein said DNA polymerase is *E. coli* DNA polymerase 1 which contains Klenow fragment activity.

47. The kit as defined in claim 41 wherein said set of chemical reagents contain acetic anhydride reagent.

48. The kit as defined in claim 41 wherein said set of chemical reagents contain alkaline acetic chloride reagent.

49. The kit as defined in claim 41 wherein said set of chemical reagents contain alkaline potassium permanganate reagent.

50. The kit as defined in claim 41 wherein said delivery method is a liposomal transfection reagent.

51. The kit as defined in claim 50 wherein said liposomal transfection reagent contains cationic liposomes.

52. The kit as defined in claim 41 wherein said first strand of nucleotide sequences is in a final concentration from about 0.1 µg/ml to about 10 µg/ml.

53. The kit as defined in claim 52 wherein said concentration is about 1.2 µg/ml to 2 µg/ml.

* * * * *